United States Patent
Britva et al.

(10) Patent No.: US 9,283,029 B2
(45) Date of Patent: Mar. 15, 2016

(54) SKIN TREATMENT USING A MULTI-DISCHARGE APPLICATOR

(75) Inventors: Alexander Britva, Migdal Ha'Emek (IL); Alexander Dverin, Herzlia (IL); Ziv Karni, Kfar Shmaryahu (IL)

(73) Assignee: ALMA LASERS LTD.

( * ) Notice: Subject to any disclaimer, the term of this patent is extended or adjusted under 35 U.S.C. 154(b) by 1478 days.

(21) Appl. No.: 11/985,939

(22) Filed: Nov. 19, 2007

(65) Prior Publication Data
US 2008/0183167 A1   Jul. 31, 2008

Related U.S. Application Data

(60) Provisional application No. 60/887,352, filed on Jan. 31, 2007.

(51) Int. Cl.
| | | |
|---|---|---|
| A61B 18/14 | (2006.01) | |
| A61B 18/04 | (2006.01) | |
| A61B 18/00 | (2006.01) | |
| A61B 18/12 | (2006.01) | |
| A61B 18/18 | (2006.01) | |

(52) U.S. Cl.
CPC .......... *A61B 18/1402* (2013.01); *A61B 18/042* (2013.01); *A61B 2018/00452* (2013.01); *A61B 2018/1213* (2013.01); *A61B 2018/1861* (2013.01)

(58) Field of Classification Search
USPC ..................................................... 606/32–52
See application file for complete search history.

(56) References Cited

U.S. PATENT DOCUMENTS

| | | | |
|---|---|---|---|
| 4,626,767 A | | 12/1986 | Clappier et al. |
| 5,129,396 A | * | 7/1992 | Rosen et al. ................. 600/407 |
| 5,300,068 A | * | 4/1994 | Rosar et al. .................... 606/34 |
| 5,383,917 A | * | 1/1995 | Desai et al. ................... 607/102 |
| 5,395,363 A | | 3/1995 | Billings et al. |
| 5,449,378 A | * | 9/1995 | Schouenborg ................. 607/46 |
| 5,976,129 A | | 11/1999 | Desai |
| 5,983,131 A | * | 11/1999 | Weaver et al. .................. 604/20 |
| 6,105,581 A | | 8/2000 | Eggers et al. |
| 6,148,232 A | | 11/2000 | Avrahami |
| 6,277,166 B2 | | 8/2001 | Zettel et al. |
| 6,518,538 B2 | | 2/2003 | Bernabei |

(Continued)

FOREIGN PATENT DOCUMENTS

| | | |
|---|---|---|
| WO | 02091934 A2 | 11/2002 |
| WO | WO2005/096980 | 10/2005 |

(Continued)

OTHER PUBLICATIONS

An International Preliminary Report on Patentability dated Dec. 23, 2010, which issued during the prosecution of Applicant's PCT/IL2007/001431.

(Continued)

*Primary Examiner* — Ronald Hupczey, Jr.

(57) ABSTRACT

A method for medical treatment includes bringing an applicator, having an array of protrusions disposed thereon, into proximity with a skin surface of a patient so as to maintain a space between a plurality of the protrusions and the skin surface. Radio-frequency (RF) electrical power is applied to the applicator so as to cause electrical discharges to be generated, in response to the RF electrical power, between the plurality of the protrusions and respective points on the skin surface via a fluid medium in the space.

24 Claims, 7 Drawing Sheets

(56) References Cited

U.S. PATENT DOCUMENTS

| | | | |
|---|---|---|---|
| 6,587,730 B2* | 7/2003 | Bernabei | 607/99 |
| 6,615,079 B1* | 9/2003 | Avrahami | 604/20 |
| 6,629,974 B2 | 10/2003 | Penny et al. | |
| 6,723,091 B2 | 4/2004 | Goble et al. | |
| 7,113,821 B1* | 9/2006 | Sun et al. | 604/21 |
| 2001/0023330 A1* | 9/2001 | Palti | 604/20 |
| 2002/0120260 A1 | 8/2002 | Morris et al. | |
| 2005/0065510 A1 | 3/2005 | Carmel et al. | |
| 2006/0189976 A1* | 8/2006 | Karni et al. | 606/41 |
| 2007/0010809 A1 | 1/2007 | Hovda et al. | |
| 2007/0208340 A1* | 9/2007 | Ganz et al. | 606/50 |

FOREIGN PATENT DOCUMENTS

| | | | | |
|---|---|---|---|---|
| WO | WO2005/096980 A1 * | 10/2005 | | A61B 18/18 |
| WO | 2006003659 A2 | 1/2006 | | |
| WO | WO2006/077567 | 7/2006 | | |

OTHER PUBLICATIONS

An International Search Report and A Written Opinion, both dated Jul. 27, 2009, issued during the prosecution of Applicant's PCT/IL2007/001431.

In corresponding patent application No. EP07827404 in Europe: search report issued Apr. 27 2012.

\* cited by examiner

SKIN TREATMENT USING A MULTI-DISCHARGE APPLICATOR

CROSS-REFERENCE TO RELATED APPLICATION

This application claims the benefit of U.S. Provisional Patent Application 60/887,352, filed Jan. 31, 2007, which is incorporated herein by reference.

FIELD OF THE INVENTION

The present invention relates generally to apparatus and methods for medical treatment, and specifically to devices for treatment of tissues using radio-frequency (RF) electrical energy.

BACKGROUND OF THE INVENTION

Various techniques and devices are known in the art for medical treatment of skin layers by application of electromagnetic energy, and in particular radio-frequency (RF) energy. The term "RF" is used broadly in the present patent application and in the claims to refer to electromagnetic waves at any frequency in the range between several kilohertz and several hundred gigahertz.

For example, PCT International Publication WO 2006/077567, whose disclosure is incorporated herein by reference, describes a system and method for heating biological tissue using RF energy. The system includes a RF source, phase shifter, impedance matching network and resonator connected to an applicator, which may be used in selective heating of cellulite bodies.

Some treatment techniques use a RF plasma discharge to deliver energy to the skin. For example, U.S. Patent Application Publication 2006/0189976, whose disclosure is incorporated herein by reference, describes a system in which a path of current from an electrode to the surface of the biological tissue to be treated is formed, thereby igniting a gas flow and forming a plasma gas-discharge. Electromagnetic interactions between the treated biological tissue and the plasma gas discharge traversing an electromagnetic interaction gap shape the profile of the plasma gas discharge. Other treatment systems using RF plasma generation are described in U.S. Pat. Nos. 6,105,581, 6,518,538, 6,629,974, and 6,723,091, whose disclosures are likewise incorporated herein by reference.

Some techniques and devices for treatment of skin layers use multi-electrode configurations to apply electrical energy to the skin at multiple points simultaneously. For example, U.S. Pat. No. 6,277,166, whose disclosure is incorporated herein by reference, describes a system and method for shrinking collagen in the dermis using a carrier with an array of electrodes. A microporous pad on the carrier, overlying the electrodes, contacts the patient's skin and ionically transports applied electromagnetic energy to ohmically heat dermal tissue beneath the epidermis. U.S. Patent Application Publication 2002/0120260, whose disclosure is incorporated herein by reference, likewise describes a tissue surface treatment apparatus in which a tissue contact surface has a plurality of apertures. Electrodes are advanced through the apertures and penetrate the skin in order to ablate tissue using RF energy.

As another example, U.S. Pat. No. 6,148,232, whose disclosure is incorporated herein by reference, describes a device for ablating the stratum corneum epidermidis of a subject. The device includes a plurality of electrodes, which are applied to the subject's skin at respective points. A power source applies electrical energy between two or more of the electrodes, in order to cause ablation of the stratum corneum for purposes of transdermal drug delivery or analyte extraction. Similarly, PCT International Publication WO 2005/096980, whose disclosure is incorporated herein by references, uses a device with a plurality of electrodes to create a pattern of perforations in one or more tissue layers.

SUMMARY OF THE INVENTION

Embodiments of the present invention that are described hereinbelow provide devices and methods for treatment of biological tissue. In these methods, multiple RF plasma discharges are created in a gap between an applicator and the surface of the tissue, such as the skin surface. The discharges are typically channeling-type discharges, having the form of streamers, arcs or sparks. The discharge parameters may be controlled so that the RF energy in each discharge is delivered to a respective treatment region below the tissue surface, thus creating a pattern of treated regions. This sort of pattern is particularly useful, for example, in ablating sub-surface skin tissue for purposes of cosmetic treatment.

In some embodiments, the RF discharges are created using a device with an applicator that comprises an applicator body, with a terminal for receiving RF electrical power. An array of protrusions is disposed on the front side of the applicator body. The front side is brought into proximity with the skin, while maintaining a space between at least a majority of the protrusions and the skin surface. As a result, RF electrical discharges are generated between the majority of the protrusions and respective points on the skin via a fluid medium (gas or liquid) in the space between the protrusions and the skin. When a gaseous medium is used, it may comprise either ambient air or another gas that is introduced into the space. The applicator is capable of creating the discharges while operating in a unipolar mode, without a dedicated ground electrode.

There is therefore provided, in accordance with an embodiment of the present invention, a medical device, including:

an applicator body, including a terminal for receiving radio-frequency (RF) electrical power; and an array of protrusions disposed on a front side of the applicator body and configured to maintain a space between at least a majority of the protrusions and a skin surface of a patient when the applicator body is brought into proximity with the skin surface so as to cause electrical discharges to be generated, in response to the RF electrical power, between the majority of the protrusions and respective points on the skin surface via a fluid medium in the space.

In one embodiment, the front side of the applicator body is convex. The protrusions are typically pointed.

Alternatively or additionally, the applicator body includes a spacer for engaging the skin surface so as to maintain the space between the protrusions and the skin surface. The spacer may be configured to seal the space against ambient air, and the device may include a fluid port communicating with the space for at least one of evacuating the space and introducing a fluid into the space.

Further alternatively or additionally, the array of protrusions is configured to generate the discharges via ambient air.

There is also provided, in accordance with an embodiment of the present invention, apparatus for medical treatment, including:

a radio-frequency (RF) power source, which is configured to generate RF electrical power; and a skin treatment device, which is coupled to receive the RF electrical power and includes an applicator, which includes an applicator body and an array of protrusions disposed on a front side of the applicator body, wherein the skin treatment device is configured to maintain a space between at least a majority of the protrusions and a skin surface of a patient when the applicator is brought into proximity with the skin surface, so as to cause electrical discharges to be generated, in response to the RF electrical power, between the majority of the protrusions and respective points on the skin surface via a fluid medium in the space.

In some embodiments, the skin treatment device is configured to be held by an operator and moved by the operator over the skin surface, and wherein the apparatus includes a cable, which connects the RF power source to the skin treatment device. Typically, the RF power source is configured to generate the RF electrical power at a predetermined frequency, and the cable has a length equal to an integer number of half-waves at the predetermined frequency. The skin treatment device may include a resonant circuit, which is tuned to the predetermined frequency.

In a disclosed embodiment, the RF power source has a predetermined impedance, which is different from a discharge impedance of the electrical discharges between the protrusions and the respective points on the skin, and the apparatus includes an impedance matching circuit, for matching the predetermined impedance to the discharge impedance. Additionally or alternatively, the RF power source includes a RF generator, which is configured to generate the RF electrical power at a constant amplitude, and a pulse-width modulation (PWM) controller, which is coupled to switch the RF generator with a variable duty cycle so as to adjust a power level of the RF electrical power that is supplied to the skin treatment device. Further additionally or alternatively, the RF power source includes a phase controller, which is operative to adjust a phase of the RF electrical power at the front side of the applicator.

In one embodiment, the RF power source and the skin treatment device are configured to generate the electrical discharges while operating in a unipolar mode.

There is additionally provided, in accordance with an embodiment of the present invention, a method for medical treatment, including:

bringing an applicator, having an array of protrusions disposed thereon, into proximity with a skin surface of a patient so as to maintain a space between a plurality of the protrusions and the skin surface; and applying radio-frequency (RF) electrical power to the applicator so as to cause electrical discharges to be generated, in response to the RF electrical power, between the plurality of the protrusions and respective points on the skin surface via a fluid medium in the space.

In one embodiment, the method includes sealing the space against ambient air, and performing at least one of evacuating the space and introducing a fluid into the space, wherein introducing the fluid may include filling the space with a gas selected from a group of gases consisting of inert gases and reactive gases. Alternatively, applying the RF electrical power includes generating the electrical discharges via ambient air.

Typically, applying the RF electrical power includes creating multiple perforations in skin tissue of the patient at the respective points. Creating the multiple perforations may cause a tightening of the skin tissue upon healing of the perforations.

There is further provided, in accordance with an embodiment of the present invention, a medical device, including:

an applicator body, including a terminal for receiving radio-frequency (RF) electrical power;

a roller, which has an axis coupled to the applicator body and has a radial surface for contacting a skin surface of a patient, and which is configured to rotate about the axis as the roller is advanced over the skin surface; and an array of protrusions disposed on the radial surface of the roller and configured to cause multiple electrical discharges to be generated, in response to the RF electrical power, in a space between the protrusions and respective points on the skin as the roller is advanced over the skin surface.

In disclosed embodiments, the roller has a shape that is selected from a group of shapes consisting of cylindrical, spherical, ellipsoidal and barrel shapes.

There is moreover provided, in accordance with an embodiment of the present invention, apparatus for medical treatment, including:

a radio-frequency (RF) power source, which is configured to generate RF electrical power; and a skin treatment device, which is coupled to receive the RF electrical power and which includes:

a roller, which has an axis and has a radial surface for contacting a skin surface of a patient, and which is configured to rotate about the axis as the roller is advanced over the skin surface; and an array of protrusions disposed on the radial surface of the roller and configured to cause multiple electrical discharges to be generated, in response to the RF electrical power, in a space between the protrusions and respective points on the skin as the roller is advanced over the skin surface.

In some embodiments, the gas is a flowing gas. Nevertheless, provisioning of a gas flow is not a requirement, and embodiments where either (i) treatment is in atmospheric condition without a gas flow; (ii) within a 'static' gas for example in a gas chamber; (iii) in a liquid for example (but not limited to) an electrolyte solution such as a saline solution (in this case, a streamer is formed and used to treat the tissue) are all within the scope of the presently disclosed technique.

There is not limitation on the shape or material of the electrodes, and there is no requirement that the electrodes have the same shape and/or same size. In one example, the shape of the electrode ends is pyramidal conical, though this is not a limitation. In some embodiments, the electrodes have a round shape or cross-section. Other exemplary electrode or pin shapes include but are not limited to semispherical, conical, and pyramidal shape. In some embodiments, the electrodes have a rectangular shape or cross section. It is noted that having an electrode with a 'sharp end' (i.e. a 'pin-like' electrode as opposed to an electrode with as opposed to a more curved end) may be useful for localizing delivered EM energy and thus localizing the plasma.

Referring once again to FIG. 8, it is noted that in general, the fill factor (see FIG. 8) or percentage of surface area that is treated may be between 1% and 99% of the treated area—i.e. there is no limitation on the specific value of this fraction. In specific embodiments, the coverage area may be between 10% and 50% of the treated area. In particular embodiments, the coverage area may be between 20% and 40% of the treated area. can vary in the range of 0.1-90%, with ranges of 0.1-1%, 1-10%, 10-30% and 30-50% for different applications.

The present invention will be more fully understood from the following detailed description of the embodiments thereof, taken together with the drawings in which:

DETAILED DESCRIPTION OF EMBODIMENTS

Figure 1:
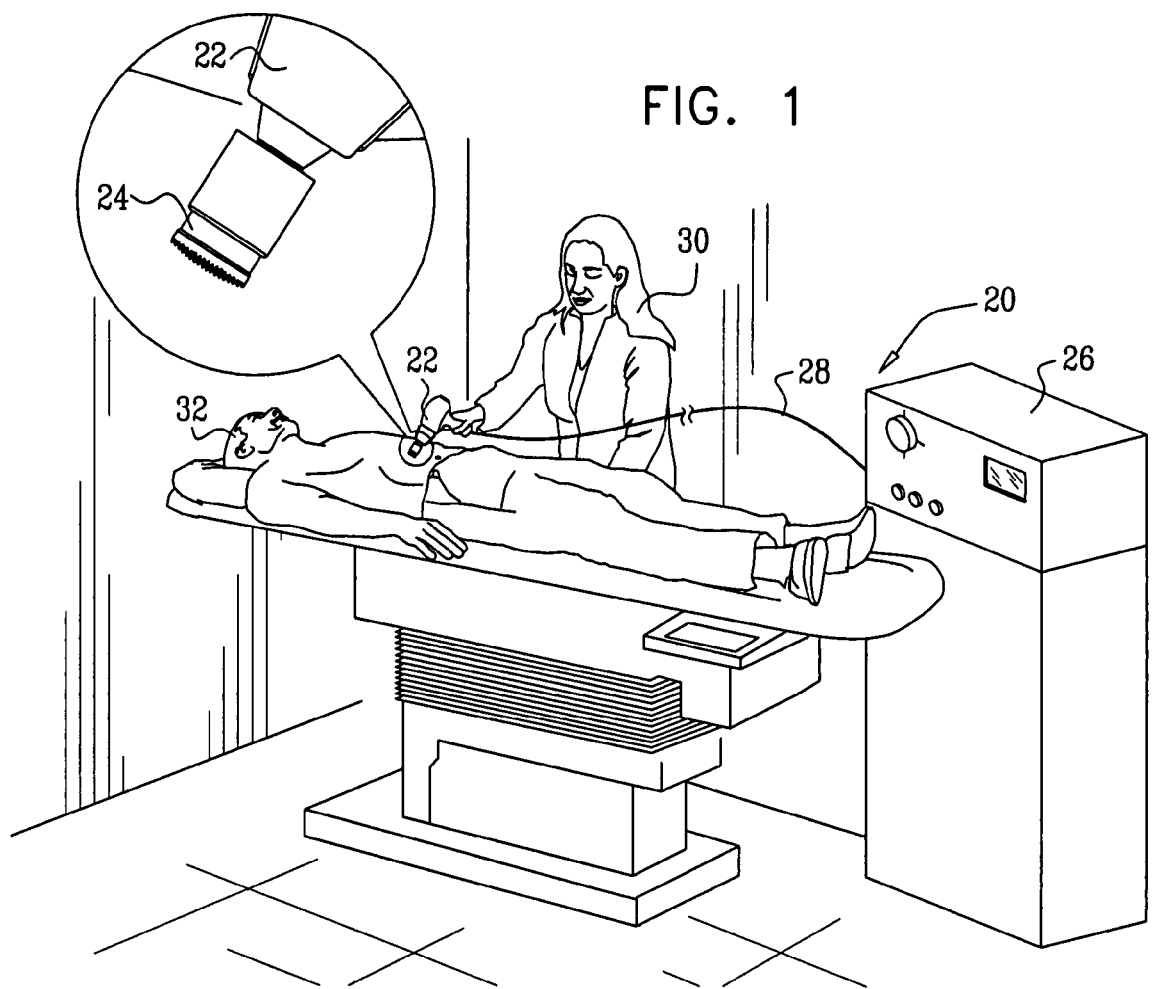
FIG. 1 is a schematic, pictorial illustration of a system for skin treatment, in accordance with an embodiment of the present invention.

FIG. 1 is a schematic, pictorial illustration of a system 20 for skin treatment, in accordance with an embodiment of the present invention. An operator 30, such as a physician, brings an applicator 24 of a skin treatment device 22 into proximity with the skin of a patient 32. A control console 26 supplies RF electrical energy to device 22 via a cable 28. The RF energy causes electrical plasma gas discharges of the channeling type to be created in the space between the front side of the applicator and the patient's skin. The discharges convey the energy to the skin surface (stratum corneum) and, particularly, to sub-surface layers of the skin, particularly the epidermis and dermis. Details of the design and operation of device 22 and applicator 24 are presented hereinbelow with reference to the figures that follow.

Application of RF energy to body tissues in system 20 is useful in a variety of medical applications. For example, device 22 may be used to ablate local regions of sub-skin tissue (dermis) for cosmetic applications, such as skin tightening and resurfacing, including treatment of fine lines, wrinkles, and acne scars. Alternatively or additionally, ablation of the outer skin layer by device 22 may be performed in conjunction with application of drug preparations to the skin for enhancing drug delivery. Further alternatively, although system 20 and the embodiments described herein are configured for skin treatment, device 22 and applicator 24 may be adapted for plasma-based treatment of the surface layers of other biological tissues. As used herein, 'treatment' refers to one or more of perforating and/or burning and/or piercing and/or denaturalization and/or coagulation and.or evaporation of tissue, for example, to a targeted depth.

Figure 2:
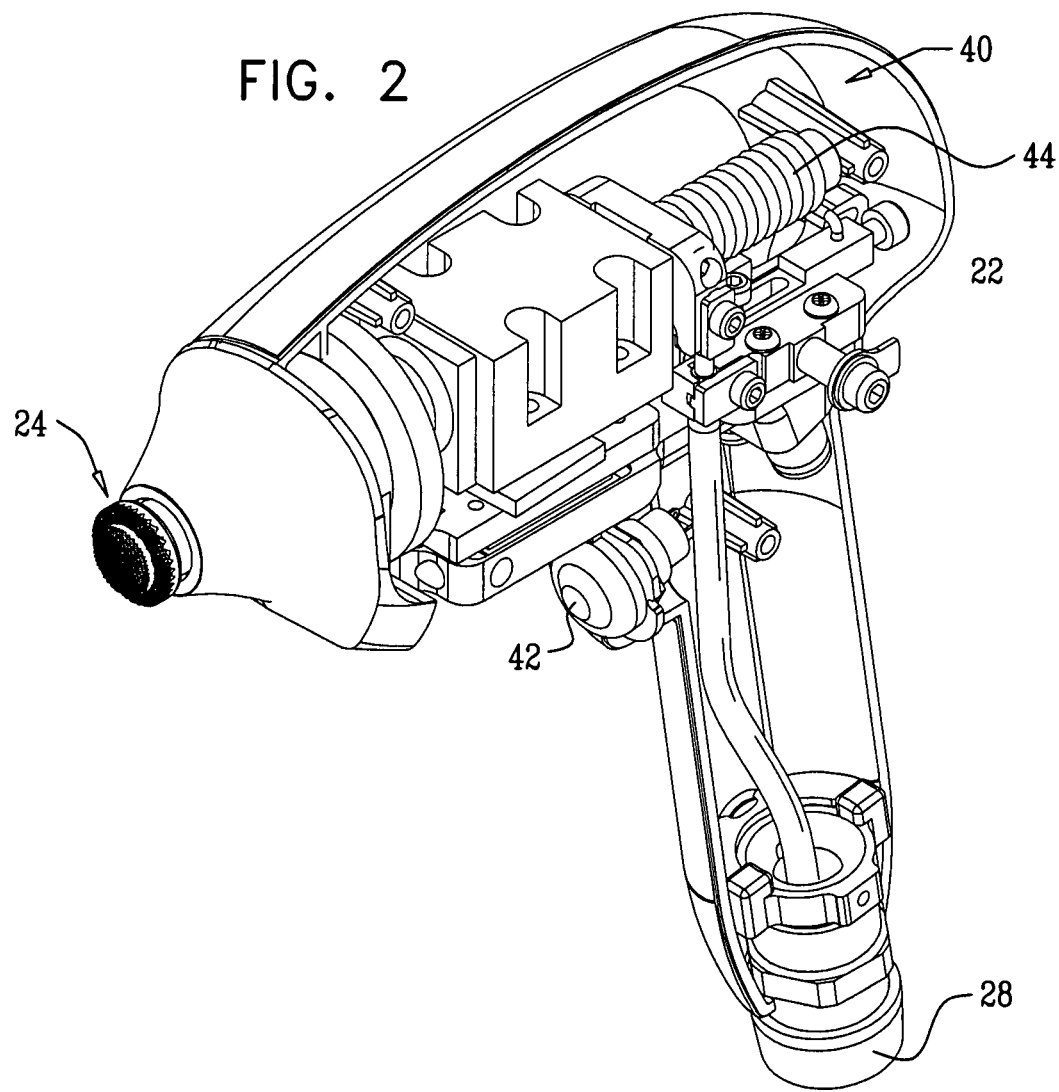
FIG. 2 is a schematic cutaway view of a device for skin treatment, in accordance with an embodiment of the present invention.
Figure 5:
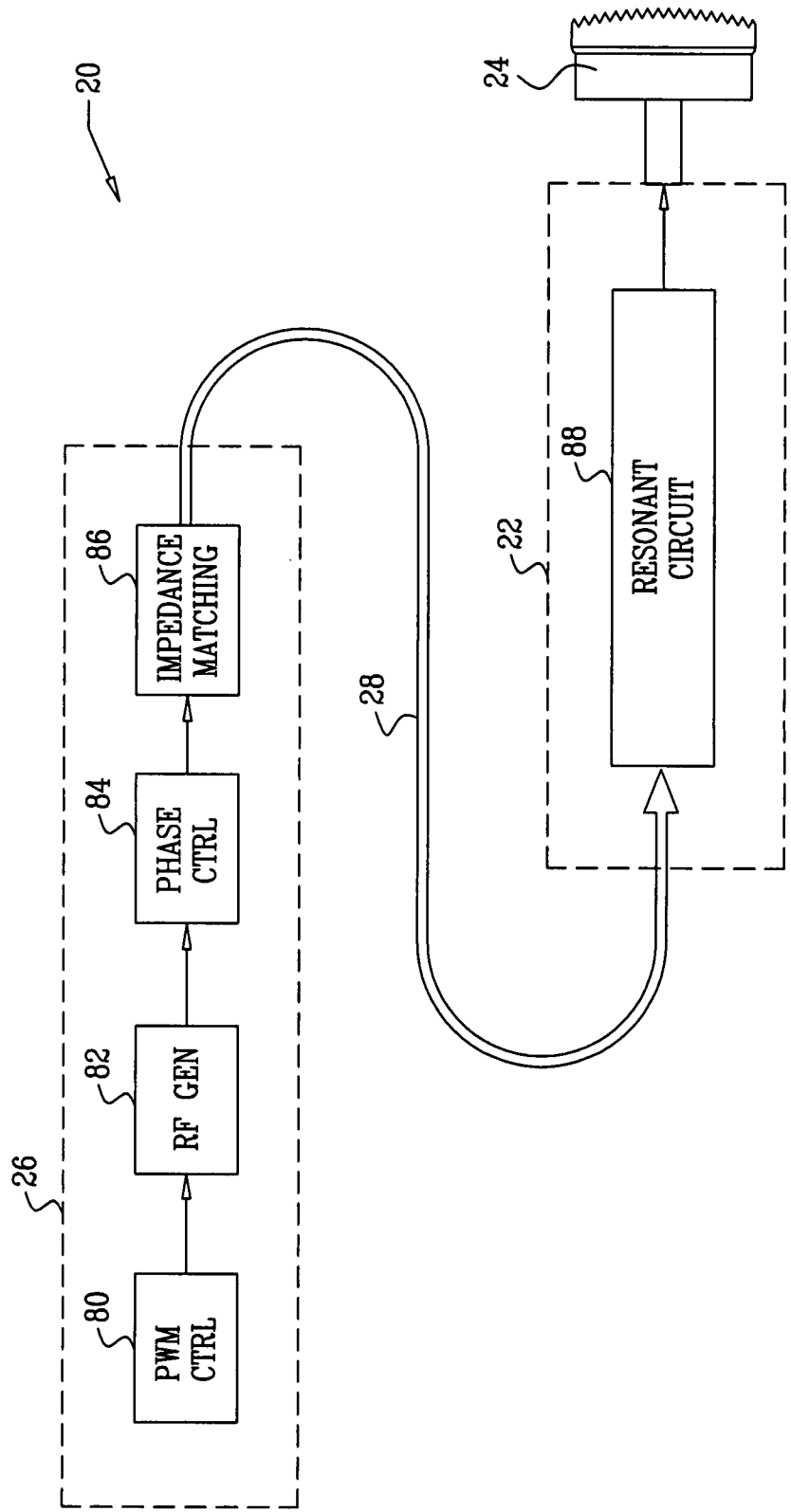
FIG. 5 is a block diagram that schematically shows electrical components of a system for skin treatment, in accordance with an embodiment of the present invention.

FIG. 2 is a schematic, cutaway view of device 22, in accordance with an embodiment of the present invention. The RF energy carried by cable 28 is fed to RF delivery circuitry 40 in device 22 when the operator presses a trigger 42. Circuitry 40 typically comprises a resonant circuit, tuned to the frequency of the RF energy. Details of these circuits are shown in FIG. 5 and described hereinbelow with reference thereto.

Careful design of circuitry 40 for the frequency and impedance characteristics of the discharges enhances the efficiency of delivery of the RF energy to the patient's skin and reduces heat dissipation. Nevertheless, to keep circuitry 40 and device 22 at a stable temperature, the device may comprise a cooler 44, which removes heat by flow of a coolant through suitable tubing. The cooler may be connected to an external pump and heat exchanger, which are controlled by a suitable temperature sensor in device 22 (not shown in the figures). The inventors have found that a water cooling system, with a water temperature of about 10-15° C., gives good results. Alternatively, a thermo-electrical cooler (TEC) may be used for this purpose. Temperature feedback may be provided to the cooling system by a thermistor attached to the ground plate of device 22.

Figure 3A:
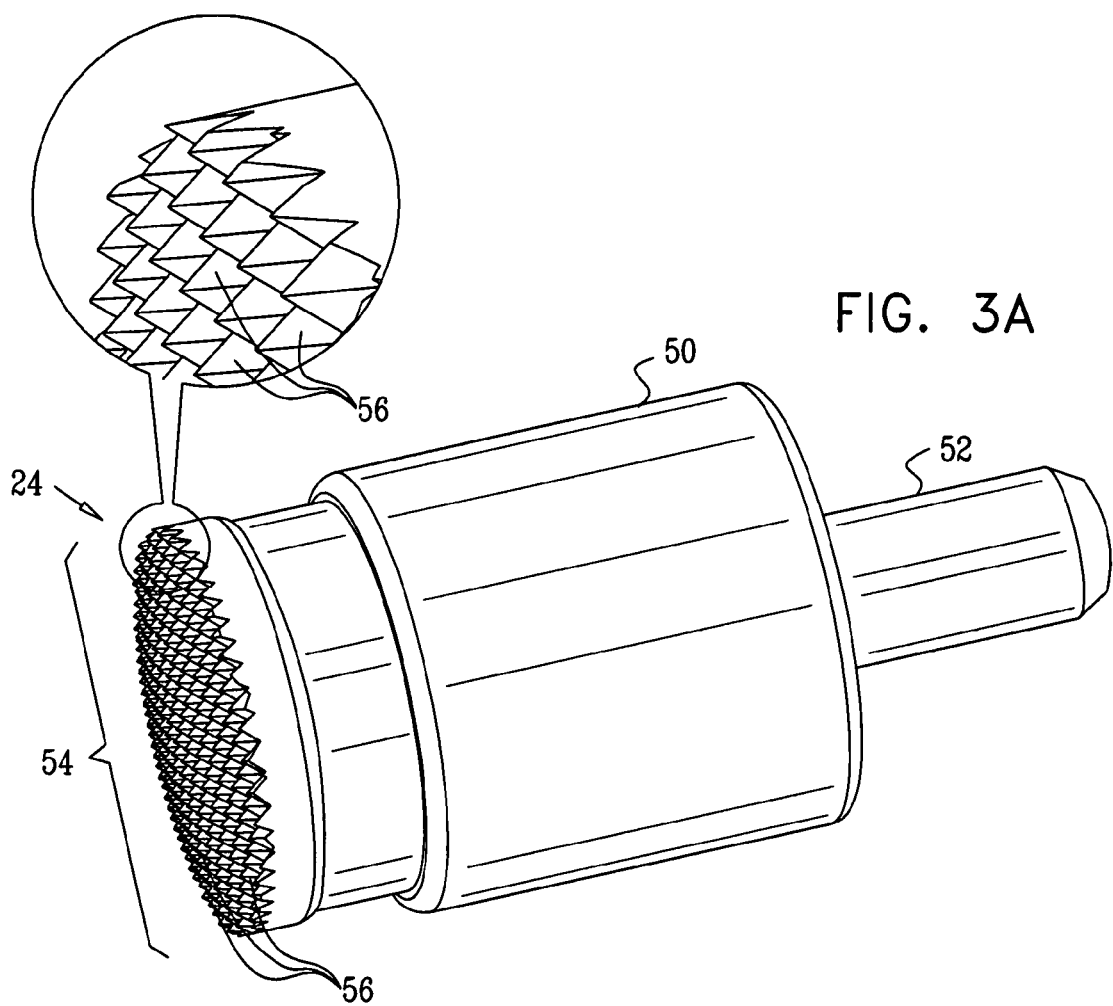
FIGS. 3A and 3B are schematic, pictorial and sectional views, respectively, of an applicator for use in the device of FIG. 2, in accordance with an embodiment of the present invention.
Figure 3B:
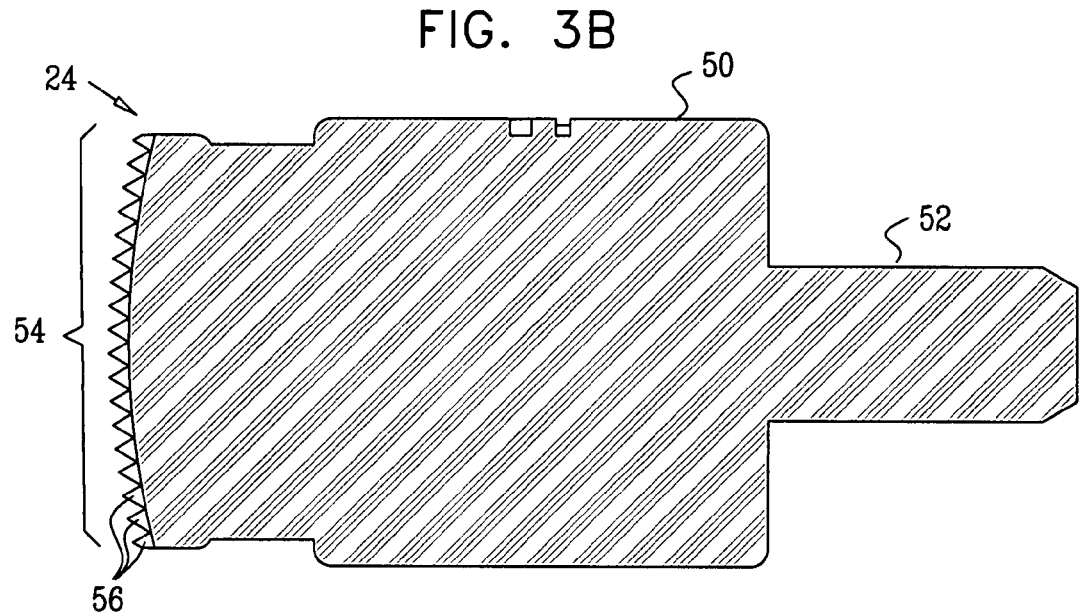

FIGS. 3A and 3B are schematic, pictorial and sectional views, respectively, of applicator 24, in accordance with an embodiment of the present invention. Typically, device 22 may be used with a variety of different, interchangeable applicators, having different geometrical, electrical and functional characteristics. A number of alternative applicator designs are described hereinbelow.

Applicator 24 comprises a body 50, having a terminal 52 that connects to circuitry 40 (FIG. 2) in order to receive RF energy. An array of protrusions 56 is formed on a front side 54 of the applicator, i.e., the side adjacent to the patient's skin when device 22 is in use. Typically, the protrusions are conical or pyramidal, as shown in FIGS. 3A and 3B, with pointed ends. The size of front side 54 and the density of protrusions 56 may be varied depending on the patient's skin type and treatment requirements. In typical dermatological applications, for example, front side 54 may have a diameter between 4 and 20 mm, while protrusions 56 are spaced between 0.5 and 2.0 mm apart. These dimensions, however, are given solely by way of example, and larger or smaller dimensions may alternatively be used.

The points at the tips of protrusions 56 concentrate the electric field and thus facilitate ignition of the electrical discharges between the protrusions and the patient's skin. For this purpose, the protrusions may alternatively have the form of pins or wires, such as those as described in the above-mentioned PCT International Publication WO 2005/096980 or other publications cited in the Background section above. In one example, the 20-100 protrusions are distributed over an area between 0.25cm^2 and 9 cm^2. Further alternatively, the protrusions may have other shapes, such as round or rectangular shapes. Although applicator 24 is pictured in FIGS. 3A and 3B as a unitary component, the applicator may alternatively comprise internal circuitry, such as capacitors and/or resistors (not shown in the figures), arranged to cause the protrusions to function as separate electrodes, and thus to assist in sustaining multiple separate discharges, in a manner similar to types of multi-sectional electrodes that are used in some gas-discharge fast flow lasers.

As can be seen in FIGS. 3A and 3B, front side 54 is convex, with a radius of curvature that is typically in the range of 20-30 mm. As a result, when operator 30 brings applicator 24 into light contact with the patient's skin (without exerting pressure against the skin), protrusions 56 will contact the skin only over a small area of front side 54. Thus, the majority of the protrusions will be spaced away from the skin by a small distance and will not be in electrical contact with the skin. Alternatively, the operator may hold applicator above the skin, so that none of the protrusions contact the skin. When RF energy is applied to the applicator, the protrusions that are not in electrical contact with the skin will ignite arc or spark discharges into the skin through the fluid (gas or liquid) medium between the protrusions and the skin.

Typically, body 50 and protrusions 56 are made from a suitable biocompatible metal, such as stainless steel. To enhance the discharge qualities, the protrusions may be coated with an additional conductive layer and/or with a non-conductive layer, such as a ceramic material or a polymer or glass. Optionally, applicator 24 may be pre-heated to facilitate ignition of the discharges.

Figure 4A:
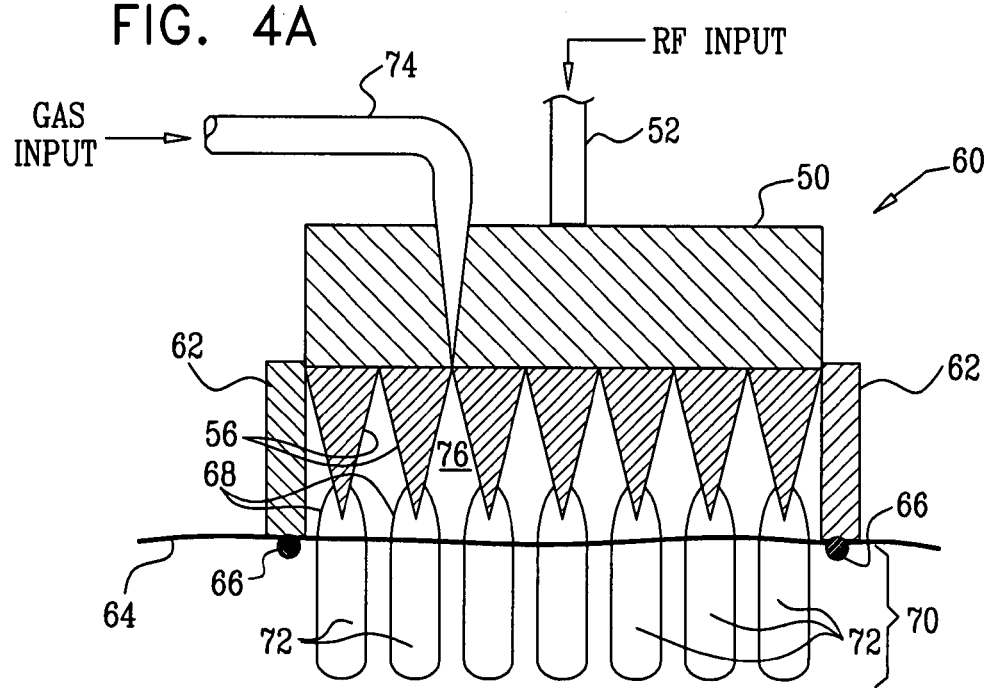
FIG. 4A is a schematic, sectional view of an applicator used in treating an area of skin, in accordance with an embodiment of the present invention.

FIG. 4A is a schematic sectional view of an applicator 60, which may be used in device 22 in place of applicator 24, in accordance with another embodiment of the present invention. The figure shows applicator 60 in contact with a surface 64 of skin 70 of patient 32. The applicator comprises protrusions 56 on the front side of applicator body 50, as in applicator 24. In this embodiment, however, applicator 60 comprises a spacer 62 in order to maintain the desired spacing between protrusions 56 and skin surface 64. The spacer in this embodiment encloses the entire array of protrusions 56, and comprises a seal 66, such as an O-ring, which inhibits the flow of air between a space 76 enclosed by the spacer and the ambient environment. Alternatively, the spacer may be configured solely for the purpose of maintaining the desired distance between the protrusions and the skin surface, while allowing air flow through the space between the protrusions and skin surface. In either case, spacer 62 is configured to maintain a certain distance between the skin surface and the tips of protrusions 56. Typically, this distance is between about 0.1 mm and 5 mm.

In different applications, the distance between the tip of electrode and the surface of the skin may range for example, from between 100 microns to 1 mm (i e the lower end of the range) up to 1-5 mm or 3-5 mm (i e the upper end of the range).

Optionally, space 76 between protrusions 56 and skin surface 64 may be filled with a selected fluid (gas or liquid) to a desired pressure via a fluid port 74. For example, the space may be filled with an inert gas that has suitable discharge-sustaining properties, such as a rare gas (such as He, Ar, Ne, Kr or Xe) or nitrogen. The gas may be filled to a pressure equal to or above atmospheric pressure, or the space may alternatively be evacuated and held at a sub-atmospheric pressure. Alternatively or additionally, a reactive gas, such as oxygen, water vapor, oxides of nitrogen or carbon, or volatile organic or inorganic gases, may be injected into space 76 for treating skin 70. Regardless of the gas composition, the gas may be stationary or may flow through space 76 during the discharge. Further alternatively, space 76 may be filled with a liquid, particularly an electrolyte, such as saline solution.

When the RF energy is applied to applicator 60 (or similarly, to the other types of applicators that are described herein), a spark is generated at each of protrusions 56, breaking down the gas in space 76 and generating a plasma discharge 68 that extends into skin 70. The discharge ablates the skin, creating a perforation 72 that extends into the subsurface layers of the skin (typically the epidermis and dermis). For effective, well-regulated ablation, it is desirable that most of the energy transferred by the applicator to the skin be conveyed by the discharge, rather than by thermal or conductive energy transfer (as would occur if protrusions 56 were in contact with the skin surface).

The depth and shape of the perforations (for example, rounded or flat bottom) may be controlled by appropriate selection of the RF discharge parameters, such as amplitude, power, frequency, phase and duration, as well as the distance of protrusions 56 from the skin. A pulse-width modulation (PWM) scheme may be used to control the delivery of RF power to the skin, as described below with reference to FIG. 6. There is no limitation on the depth or diameter of the hole formed. In exemplary embodiments, the holes having a depth between 10 micron and 200 microns is formed. In typical cosmetic treatment applications, the perforations are made about 100-150 μm deep and 80-120 μm in diameter, but the inventors have found that clean, well-controlled perforations may be created in the manner described above to a depth of at least 300 μm. Alternatively, the perforations may be made wider and shallower.

In operation of system 20, operator 30 typically moves device 22 so that the applicator scans over an area of the skin that is to be treated. At each location in the area, the operator actuates the device for a short time, typically on the order of 100-200 ms at a RF power level between 30 and 80 W. Alternatively, longer exposure times at lower power may be used, and vice versa. Depending on the skin type and condition being treated, the operator may make only a single pass or several passes over the area.

Figure 4B:
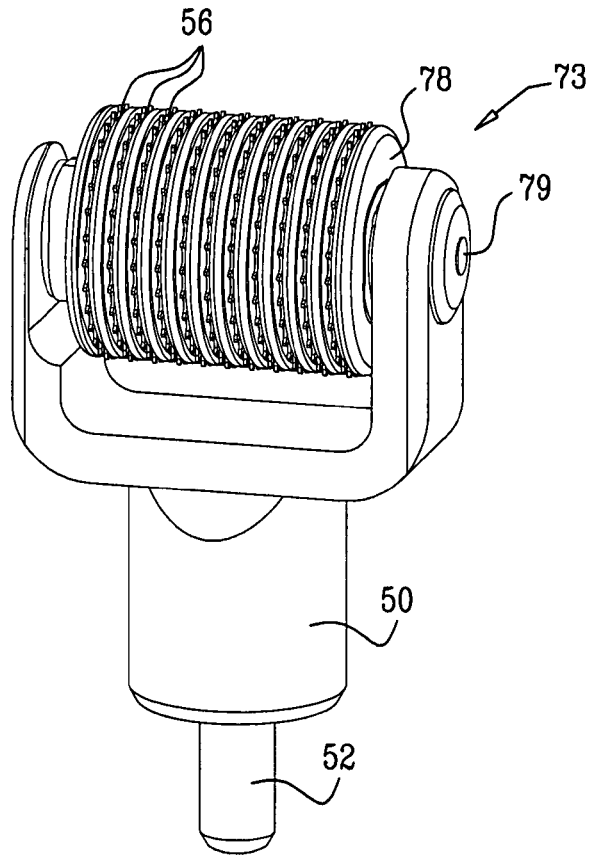
FIG. 4B is a schematic, pictorial view of an applicator used in treating an area of skin, in accordance with another embodiment of the present invention.

FIG. 4B is a schematic, pictorial illustration of an applicator 73, in accordance with another embodiment of the present invention. Applicator 73 comprises a roller 78, which has multiple protrusions 56 on its radial surface. The roller may be cylindrical, as shown in FIG. 4B, or may have any other suitable shape, such as a spherical, ellipsoidal or barrel shape. Roller 78 is mounted to rotate on an axis 79, so as to roll over the area under treatment. Typically, the roller is advanced over the skin at a speed between 1 and 10 mm/sec. As the roller advances, protrusions 56 alternately contact the skin and move away from the skin. When a given protrusion is near the skin, but not in direct contact, a discharge is ignited between that protrusion and the skin.

FIG. 5 is a block diagram that schematically shows electrical components of system 20, in accordance with an embodiment of the present invention. Console 26 comprises a RF generator 82, which generates RF energy at a desired frequency. For skin treatment, the inventors have found that RF energy at about 40 MHz (typically at 40.68 MHz) gives good results. In some embodiments, the energy short-wave energy, for example, having a frequency selected from the group consisting of 13.56, 27.13 and 40.68 MHz. Alternatively, the components of system 20 may be adapted to operate at higher or lower frequencies, from the kilohertz to the gigahertz range. RF generator 82 typically comprises an oscillator and amplifier, which may be of any suitable type, such as a cascade amplifier with a Pierce-type oscillator, as described, for example, in U.S. Pat. No. 4,626,767, whose disclosure is incorporated herein by reference. To give a pure sinusoidal output, the final stage of the RF generator may comprise a matched pair of transistors in a push/pull configuration.

In one embodiment, RF generator 82 outputs approximately 300-400 W into a 50Ω resistive load, with minimal reflected RF power. To maintain good impedance matching, the amplitude of the RF wave output by the RF generator should be held roughly constant. As noted above, however, it is often necessary to adjust the amount of RF power this is delivered to the patient's skin to a considerably lower level. For this purpose, the RF generator is switched by a pulse-width modulation (PWM) controller 80, and the average power output of the RF generator is thus controlled by modulating the duty cycle while maintaining constant RF amplitude during the RF pulses.

Figure 6:
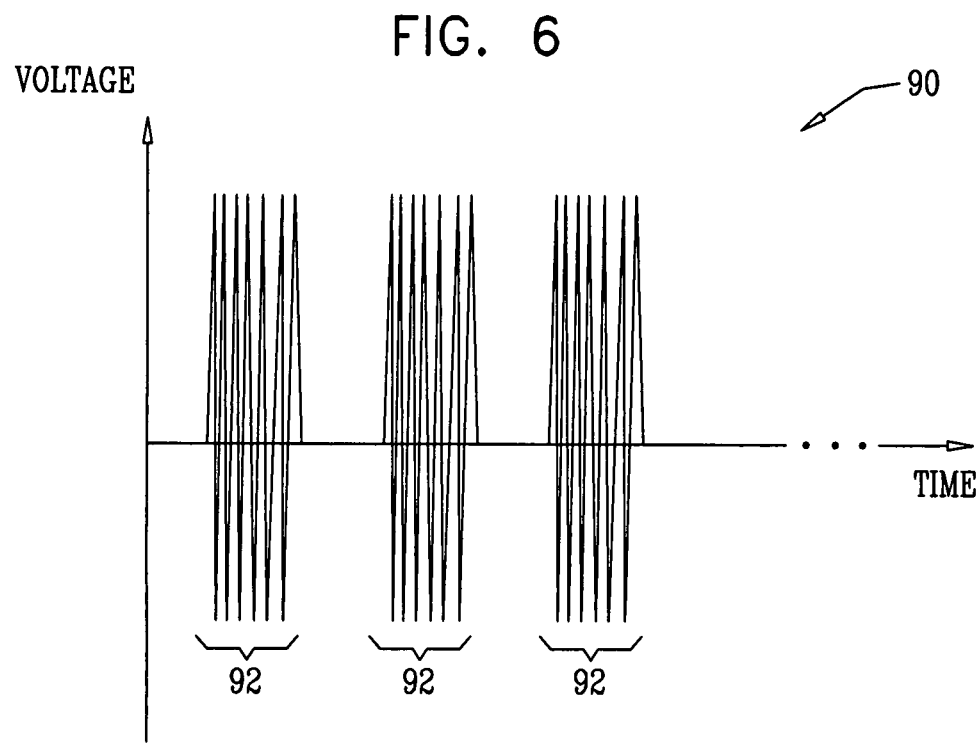
FIG. 6 is a schematic plot showing a pattern of application of RF energy over time by a system for skin treatment, in accordance with an embodiment of the present invention.

FIG. 6 is a schematic plot showing a pattern 90 of output of RF energy over time by RF generator 82, in accordance with an embodiment of the present invention. PWM controller 80 modulates the RF generator on and off with rectangular pulses at a frequency that is considerable less than the RF frequency, thus generating a sequence of RF pulses 92. The PWM controller may be used to generate substantially any desired duty cycle (and thus any desired average power output from the RF generator, up to the full output power at 100% duty cycle). The inventors have found that operating PWM controller 80 at a modulation frequency between 10 and 100 Hz, with duty cycle between 5% and 30%, gives good results in typical skin treatment applications. For example, the PWM controller may be operated at a frequency of 20-25 Hz, and the PWM duty cycle controlled so that average RF power between about 30 and 70 W is applied to the skin. Power settings between 45 and 55 W, with application of the RF energy for about 0.1 sec at each location that is treated, have been found to give good results in cosmetic skin treatment.

Returning now to FIG. 5, console 26 optionally comprises a phase controller 84, for applying a variable phase shift to the output RF energy. The phase controller may comprise, for example, a trombone line, which is a transmission line that may be mechanically lengthened and shortened to vary the output phase. The phase controller may be used to determine the phase of the RF wave at the output from applicator 24, and thus to vary the depth beneath the patient's skin at which the RF electric field is maximized. As a result, it may be possible to selectively ablate, denature or coagulate tissue in the collagen at multiple points beneath the skin surface, while minimizing damage to the outer skin layer. Subsequent healing in the collagen tightens and smoothens the skin.

Alternatively or additionally, the length of cable 28 may be calibrated to give a known, fixed relation between the phase of the RF wave at the output from RF generator 82 and the phase of the wave received over the cable at device 22. For example, the cable may be cut to a length that is equal to an integer number of half-waves at the RF frequency, i.e., $L=n\lambda/2$, wherein L is the length of the cable, $\lambda$ is the RF wavelength, and n is an integer.

Console 26 outputs the RF energy to cable 28 via an impedance matching circuit 86. As noted earlier, the characteristic impedance of applicator 24 (together with resonant circuit 88 and the body tissue adjacent to the applicator) is typically in the range of 260-320Ω. Circuit 86 is thus designed to match the 50Ω output impedance of the RF generator to a 300Ω load impedance, so that the RF energy is delivered efficiently to the patient's skin with minimal reflection.

Figure 7:
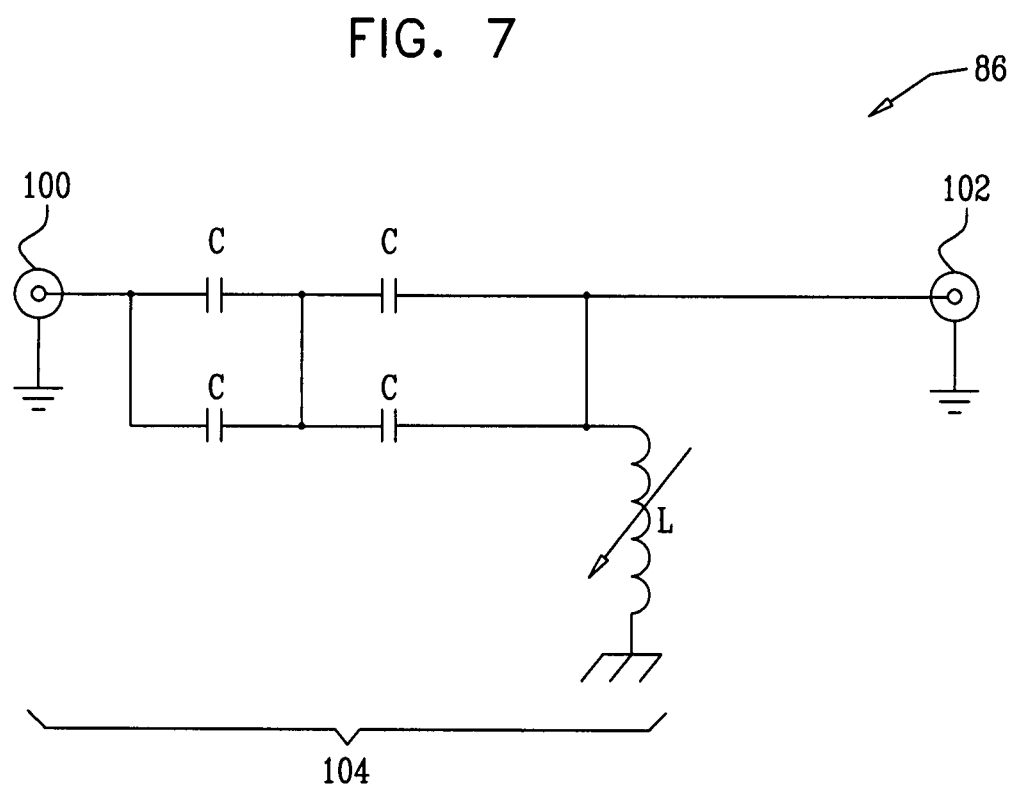
FIG. 7 is an electrical schematic diagram of an impedance matching circuit, in accordance with an embodiment of the present invention.

FIG. 7 is an electrical schematic diagram of impedance matching circuit 86, in accordance with an embodiment of the present invention. Circuit 86 in this example comprises a network 104 of capacitors (C) and a variable inductor (L) arranged between coaxial input and output terminals 100 and 102. To match the 50Ω input impedance to the 300Ω load impedance at the 40.68 MHz operating frequency of system 20, C=33 pF for all four capacitors, and L=400 nH. Alternatively, other network types and component values may be used depending on application requirements.

When cable 28 is cut to a length that is equal to an integer number of half-waves ($L=n\lambda/2$, as explained above), the cable is "impedance-transparent," and the output of impedance matching circuit 86 is effectively coupled directly to device 22, as though there were no intervening cable. The real impedance (active resistance) of the cable at 40.68 MHz is typically about 2 kΩ, which is significantly higher than the impedance of the skin tissue (260-320Ω). The cable thus serves as a ballast resistor, dissipating 5-8% of the energy delivered from the RF generator.

Returning to FIG. 5, the RF energy from cable 28 is conveyed to applicator 24 via a parallel resonant circuit 88, which is tuned to the frequency of RF generator 82. The resonant circuit comprises a variable inductor, with typical inductance of 2200 nH, coupled with the parasitic capacitance of the structure of device 22, which is roughly 7 pF. The real impedance of resonant circuit 88 is typically in the range of 5-15 kΩ. The capacitance (and hence the resonant frequency of circuit 88) varies with temperature. Cooling of the circuits in device 22, as described above, is thus useful in preventing changes in the resonant frequency during use of the device.

As noted earlier, the therapeutic effects of system 20 depend on the characteristics of the discharge created by applicator 24, which in turn depend on parameters such as the RF power, phase, exposure duration and distance of the applicator from the skin. These parameters may be controlled directly by operator 30. Alternatively or additionally, console 26 may comprise a computerized controller (not shown), which sets the parameters automatically based on treatment information provided by the operator. Optionally, the computerized controller may receive feedback from the treatment site, such as a laser measurement of the depth of the perforations created in the patient's skin, and may adjust the treatment parameters accordingly.

Optionally, the multi-point electrical discharge generated by device 22 may be used in conjunction with other treatment modalities. For example, the discharge-based methods described above may be used in conjunction with optical and/or ultrasonic therapies for enhanced therapeutic results.

In some embodiments, the aforementioned technique is carried out such that certain treatment regions are formed (i.e. at the surface or at a given depth) which are surrounded by untreated regions (or differently treated regions). When this is carried out, for example with a matrix or lattice of electrodes, a pattern is created on the treated biological tissue.

The heated gas and/or plasma-gas discharge may be useful for coagulating and/or evaporating the biological tissue, and may create a series of perforations or holes in the tissue (for example skin) to a given depth or depths. This may be useful for cosmetic applications (for example, skin rejuvenation such as skin resurfacing or skin tightening) and for drug delivery via the perforations.

Figure 8:
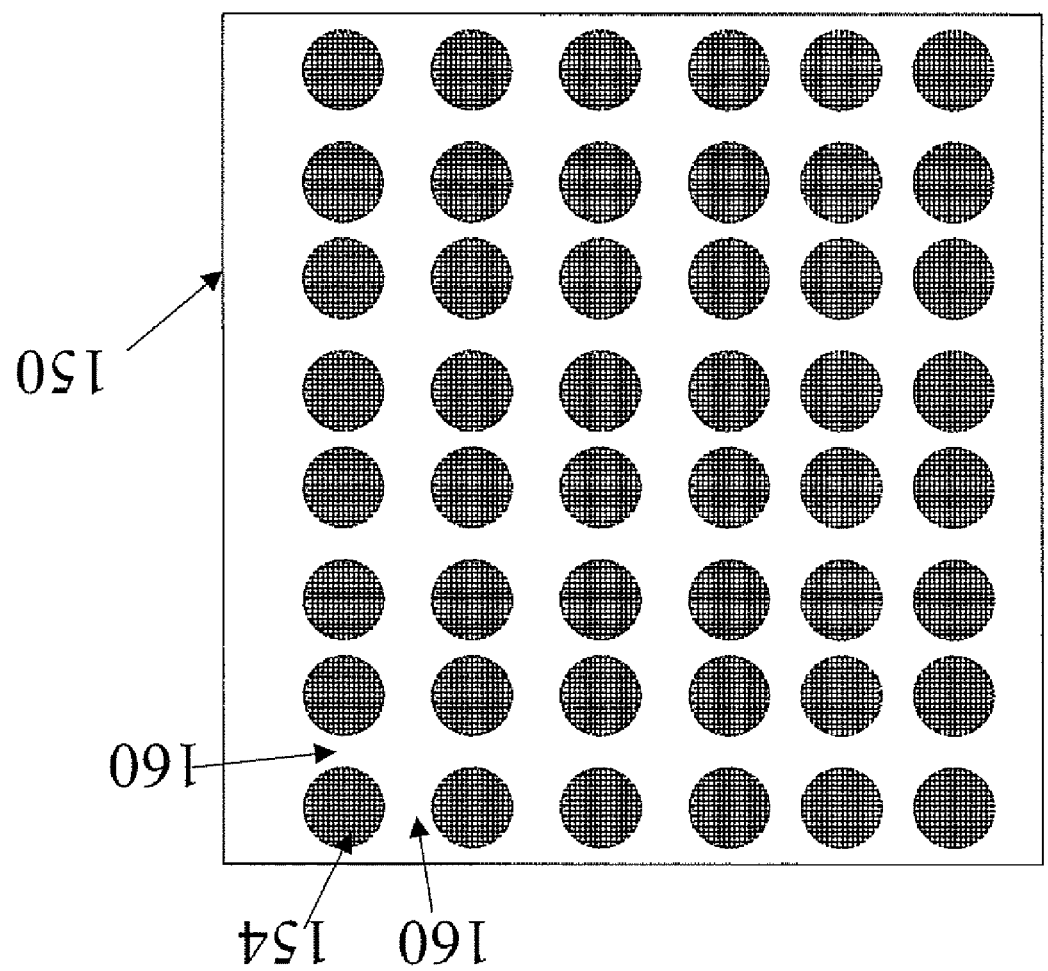
FIG. 8 illustrates a treatment pattern where each of a plurality of 'treated regions' is surrounded by an 'untreated' (or differently treated) region on the surface of biological tissue.

An exemplary treatment pattern is illustrated, for example, in FIG. 8 which illustrates a treatment pattern where each of a plurality of 'treated regions' 154 is surrounded by an 'untreated' (or differently treated) region 160 on the surface 150 of biological tissue, for example skin.

For each electrode, the plasma-gas discharge heats biological tissue (preferably but not limited to skin) in the vicinity of the tissue, thereby producing a plurality of holes or damage sites.

Referring once again to FIG. 8, it is noted that in general, the fill factor (see FIG. 8) or percentage of surface area that is treated may be between 1% and 99% of the treated area —i.e. there is no limitation on the specific value of this fraction. Thus, in some embodiments, the coverage area. In specific embodiments, the coverage area may be between 10% and 50% of the treated area. In particular embodiments, the coverage area may be between 20% and 40% of the treated area. can vary in the range of 0.1-90%, with ranges of 0.1-1%, 1-10%, 10-30% and 30-50% for different applications.

Furthermore, it is noted that the lattice patterns in FIG. 8 and shape of treatment areas (154) and differently-treated or untreated areas (160) is intended as exemplary and not as limiting.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for perforation, denaturalization or coagulation of skin, comprising:
a radio-frequency (RF) power source, which is configured to generate RF electrical power; and
a skin treatment device, which is coupled to receive the RF electrical power and which comprises:
a roller, which has an axis and has a radial surface for contacting a skin surface of a patient, and which is configured to rotate about the axis as the roller is advanced over the skin surface; and
an array of protrusions disposed on the radial surface of the roller and configured so that when at least some of the protrusions are non-contact protrusions that are not in contact with the skin surface, the non-contact protrusions ignite gas in an intervening space between the noncontact protrusions and the skin surface, in response to the RF electrical power, so as to generate multiple electrical discharges, while operating in a unipolar mode, between the protrusions and respective points on the skin as the roller is advanced over the skin surface, wherein the apparatus is operative to generate the multiple electrical discharges in a manner that forms perforations each having a depth of between 10 microns and 150 microns at each of the respective points on the skin, and wherein:
i. the RF power generated by the RF power source, received by an applicator body and employed to trigger ignition of the gas has a frequency that is in an ISM radio band centered at 13.56 MHz, 27.13 MHz, or 40.68 MHz and/or
ii. the device further comprises a phase controller configured to vary and output phase of the RF electrical power received by the applicator body and employed to trigger ignition of the gas.

2. The apparatus according to claim 1, wherein the skin treatment device is configured to be held by an operator and moved by the operator over the skin surface, and wherein the apparatus comprises a cable, which connects the RF power source to the skin treatment device, and wherein the cable has a length equal to an integer number of half-waves of an operating frequency of the RF power source.

3. The apparatus according to claim 2, wherein the skin treatment device comprises a resonant circuit, which is tuned to a predetermined frequency.

4. The apparatus according to claim 1, wherein the RF power source has a predetermined impedance, which is different from a discharge impedance of the electrical discharges between the protrusions and the respective points on the skin, and wherein the apparatus comprises an impedance matching circuit, for matching the predetermined impedance to the discharge impedance.

5. The apparatus according to claim 1, wherein the RF power source comprises a RF generator, which is configured to generate the RF electrical power at a constant amplitude, and a pulse-width modulation (PWM) controller, which is coupled to switch the RF generator with a variable duty cycle so as to adjust a power level of the RF electrical power that is supplied to the skin treatment device.

6. The apparatus of claim 1 wherein the RF power generated by the RF power source, received by the applicator body and employed to trigger ignition of the gas has a frequency that is in an ISM radio band centered at 13.56 MHz, 27.13 MHz, or 40.68 MHz.

7. A method for perforation, denaturalization or coagulation of skin, comprising:
forming a plurality of perforations having depths that each have a depth of between 10 microns and 150 microns in a skin surface of a patient by:
a. bringing an applicator, having an array of protrusions disposed thereon, into proximity with the skin surface so as to maintain an intervening space between at least some of the protrusions and the skin surface, the at least some protrusions being non-contact protrusions that are not in contact with the skin surface; and
b. applying radio-frequency (RF) electrical power having an RF frequency that is in an ISM radio band centered at 13.56 MHz, 27.13 MHz, or 40.68 MHz to the applicator so that the non-contact protrusions, in response to the RF power, ignite gas in the intervening space so as to:
i. generate electrical discharges, while operating in a unipolar mode, between the non-contact protrusions and respective points on the skin surface; and
ii. subject the skin surface to the generated electrical discharges so as to form the plurality of perforations having depths that each have a depth of between 10 microns and 150 microns.

8. The method according to claim 7, wherein the applicator comprises a roller having a radial surface on which the array of protrusions is disposed, and wherein bringing the applicator into proximity with the skin surface comprises rolling the roller over the skin surface.

9. The method according to claim 7, wherein creating the multiple perforations causes a tightening of the skin tissue upon healing of the perforations.

10. The method according to claim 7, wherein applying the RF electrical power comprises providing the RF electrical power from an RF power source to the applicator via a cable having a length equal to an integer number of halfwaves at the RF frequency.

11. The method according to claim 7, wherein an RF power source from which the radio-frequency (RF) electrical power is applied has a predetermined impedance, which is different from a discharge impedance of the electrical discharges between the protrusions and the respective points on the skin, and wherein providing the RF electrical power comprises matching the predetermined impedance to the discharge impedance using an impedance-matching circuit between the RF power source and the applicator.

12. The method according to claim 7, wherein applying the RF electrical power comprises adjusting a phase of the RF electrical power where the electrical discharges are generated.

13. The method of claim 7 wherein the perforations are each between 80 microns and 120 microns in diameter.

14. The method of claim 7 wherein the depths of the perforations are each at least 100 microns.

15. The method of claim 14 wherein the perforations are each between 80 microns and 120 microns in diameter.

16. The method of claim 7 wherein:
i. the treatment is carried out to create a pattern of plurality of discrete damage sites within a region of skin, the damage sites being separated by differently treated or untreated areas within the region of skin; and
ii. an aggregate area of the damage sites is between 1% and 10% of the region of skin.

17. The method of claim 16 wherein the pattern is a lattice pattern.

18. The method of claim 16 wherein 20-100 of the protrusions are distributed over an area between 0.25 cm^2 and 9 cm^2.

19. A method for perforation, denaturalization or coagulation of skin, comprising:
   forming a plurality of perforations having depths that each have a depth of between 10 microns and 150 microns in a skin surface of a patient by:
      bringing an applicator, having an array of protrusions disposed thereon, into proximity with the skin surface so as to maintain an intervening space between at least some of the protrusions and the skin surface, the at least some protrusions being non-contact protrusions that are not in contact with the skin surface;
      generating radio-frequency (RF) electrical power at a frequency that is in an ISM radio band centered at 13.56 MHz, 27.13 MHz, or 40.68;
      employing a phase controller to vary an output phase of the RF electrical power;
      applying the variable phase radio-frequency (RF) electrical power to the applicator so that the non-contact protrusions, in response to the RF power, ignite gas in the intervening space so as to:
         i. generate electrical discharges, while operating in a unipolar mode, between the non-contact protrusions and respective points on the skin surface; and
         ii. subject the skin surface to the generated electrical discharges so as to form the plurality of perforations having depths that are each between 10 microns and 150 microns.

20. The method of claim 19 wherein varying of the output phase varies a depth beneath the patient's skin at which an intensity of the RF electrical power is maximized.

21. The method of claim 19 wherein the depths of the perforations are each at least 100 microns.

22. A method for perforation, denaturalization or coagulation of skin, comprising: identifying a patient having a skin condition selected from the group consisting of fine lines, wrinkles, and scars;
   treating the skin condition by forming a plurality of perforations in a skin surface of the patient at a location of the lines, wrinkles of scars, the perforations each having depths of between 10 microns and 150 microns, the formation of the perforations in the skin surface and the subsequent healing thereof being effective to treat the skin condition, wherein the formation of the perforations having the depths of between 10 microns and 150 microns comprises:
      bringing an applicator, having an array of protrusions disposed thereon, into proximity with the skin surface so as to maintain an intervening space between at least some of the protrusions and the skin surface, the at least some protrusions being non-contact protrusions that are not in contact with the skin surface; and
      applying radio-frequency (RF) electrical power at a frequency that is in an ISM radio band centered at 13.56 MHz, 27.13 MHz, or 40.68 MHz to the applicator so that the non-contact protrusions, in response to the RF power, ignite gas in the intervening space so as to:
         i. generate electrical discharges, while operating in a unipolar mode, between the non-contact protrusions and respective points on the skin surface; and
         ii. subject the skin surface to the generated electrical discharges so as to form the plurality of perforations having depths that of between 10 microns and 150 microns.

23. The method of claim 22 wherein the condition is a presence of acne scars which are treated by the formation of the perforations and subsequent healing thereof.

24. The method of claim 22 wherein a depth of each of the perforations is at least 100 microns.

* * * * *